United States Patent [19]
Cook et al.

[11] Patent Number: 5,223,618
[45] Date of Patent: Jun. 29, 1993

[54] 4'-DESMETHYL NUCLEOSIDE ANALOG COMPOUNDS

[75] Inventors: Philip D. Cook, Carlsbad; Yogesh S. Sanghvi, San Marcos, both of Calif.

[73] Assignee: ISIS Pharmaceuticals, Inc., Carlsbad, Calif.

[21] Appl. No.: 566,836

[22] Filed: Aug. 13, 1990

[51] Int. Cl.$^5$ .................................... C07D 473/00
[52] U.S. Cl. .................. 544/276; 544/242; 544/245; 544/264; 544/277; 544/311; 544/314; 544/317; 536/27.14; 536/28.54
[58] Field of Search ................. 536/27, 28, 29; 544/276, 277; 514/47, 48, 50, 51, 244, 243

[56] References Cited
U.S. PATENT DOCUMENTS
4,591,614 5/1986 Miller et al. ..................... 536/27

FOREIGN PATENT DOCUMENTS
WO89/12060 12/1989 PCT Int'l Appl. .

OTHER PUBLICATIONS
C. R. Johnson, et al., Tetrahedron Letters, 28, 4131–4134, (1987).
A. K. Biggadike, et al., Journal Chemical Society, Chemical Communication, 458 (1990).
T. Atkinson and M. Smith (Oligonucleotide Synthesis. A Practical Approach. M. J. Gait, Ed., IRL Press, Washington, D.C., 1985, p. 49).
M. Matteucci, Deoxyoligonucleotide Analogs Based On Formacetal Linkages. Tetrahedron Letters, vol. 31, 17:2385–2388, 1990.
J. M. Coull, D. V. Carlson and H. L. Weith. Synthesis And Characterization Of A Carbamate-Linked Oligonucleoside. Tetrahedron Letters, vol. 28, pp. 745–748.
E. P. Stirchak et al., Uncharged Stereoregular Nucleic Acid Analogues. 1. Synthesis of a Cytosine-Containing Ogligomer with Carbamate Internucleoside Linkages. J. Org. Chem., vol. 52 pp. 4202–4206, 1987.

*Primary Examiner*—Johnnie R. Brown
*Assistant Examiner*—J. Oliver Wilson
*Attorney, Agent, or Firm*—Woodcock Washburn Kurtz Mackiewicz & Norris

[57] ABSTRACT

Novel oligonucleotide analogs are provided having improved cellular uptake, improved resistance to nucleases, and good hybridization to target RNA. Such analogs are provided having substantially non-chiral, non-ionic linking functionalities between the sugars and sugar analogs thereof. In accordance with preferred embodiments, the 4' position of a sugar or sugar analog at one nucleoside is linked to the 3' position of a second sugar or sugar analog of a second nucleoside by a linking function that comprises a two- or three- carbon backbone chain. In accordance with preferred embodiments, the linking functions comprise the formula)—R-$_1$—O where R$_1$ comprises a two or three carbon backbone. Such linking functions also, preferably comprise ether functionalities to effect such linkage. Processes for the automated synthesis of oligonucleotide analogs are also provided.

6 Claims, 1 Drawing Sheet

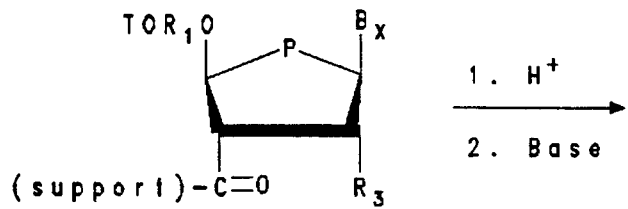 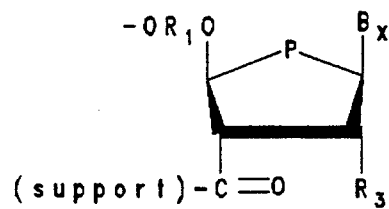
FIGURE 1A          FIGURE 1B
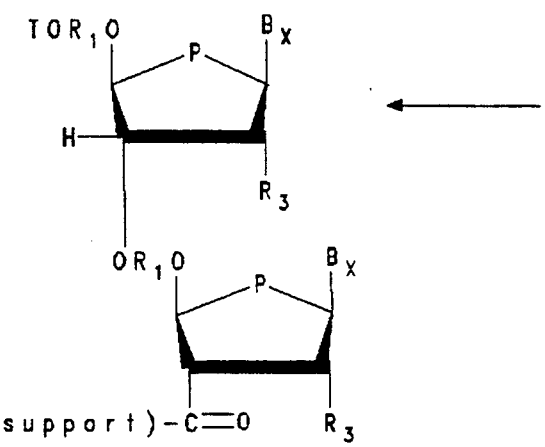 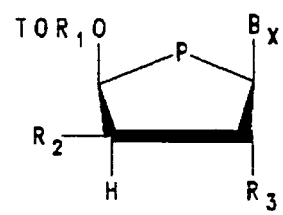
FIGURE 1D          FIGURE 1C
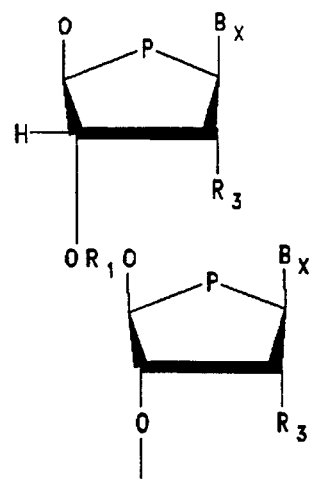
FIGURE 2

4'-DESMETHYL NUCLEOSIDE ANALOG COMPOUNDS

FIELD OF THE INVENTION

This invention is directed to novel oligonucleoside analogs, to components thereof and to methods for their formulation and use. Such oligonucleoside analogs have wide utility including therapeutics, diagnostics and in reagents for research.

BACKGROUND OF THE INVENTION

It has been known to modify nucleosides, nucleotides, and certain oligonucleotides for various purposes. Included among such known modifications are modifications to the groups linking the sugar moieties of said nucleic species. Thus, it has been known to alter the phosphodiester bonds naturally extant in nucleic acids to provide what has been perceived to be improved structures, especially structures which have improved cell uptake. A number of such modifications are known including phosphothioates, substituted phosphonates and others. The general synthetic scheme for arriving at such analogs has been to involve the 5'-hydroxyl group of a nucleoside or its nucleotide, either bound to a polymeric carrier or to a sequence-specified 3'-nucleotide with its phosphorus atom in either the pentavalent or trivalent oxidation state. Specific coupling procedures have been referred to as the phosphorus triester, the phosphorus diester, the phosphite triester, and the hydrogen phosphonate phosphorylation procedures. Commercially available monomers and polymeric carrier-bound monomers are available for such methods having protective basis (G, A, C, T, U and other heterocycles) along with protected phosphorus atoms to allow storage and prevent non-specific reactions during the coupling process. Catalysts for enhancing the electrophilicity of the 5'-hydroxyl group are not required but are available.

Synthesis of non-ionic methyl phosphonates and ionic phophorothioates are similarly known and both oligonucleotide analog classes are currently receiving attention as gene modulating agents. Such prior attempts at modifying the intersugar linking groups have found some promise in therapeutics and the like however each exhibits substantial shortcomings. Thus, with linkages such as methyl phosphonate diester linkages, chirality is introduced into the system. Since the different forms of such chiral materials are generally absorbed into cells at different rates, the different forms of such materials are believed to lead to less-than-optimum performance.

Other materials, including the naturally-occurring phosphodiester forms, exhibit an ionized condition which is believed to interfere with cell absorption. It is believed that substantially non-ionic materials will be absorbed more readily by cells and be more effective in therapeutics and the like.

Both the methyl phosphonate and phosphorothionate modifications of oligonucleotides are believed to impart nuclease resistance, to enhance to some degree cellular transport of oligomers and to strengthen hybridization binding of the oligomer to target nucleic acid sequences. However, still greater improvement in these qualities is required before effective therapeutics, diagnostics, and research tools become available. Accordingly, there is a long-felt need for improved oligonucleotide analogs, for corresponding component nucleosides, and for compositions useful for the formulation of oligonucleotide analogs which, at once, are substantially non-chiral and non-ionic. Such materials, which are provided in accordance with the present invention, are believed to lend superior qualities of cell uptake, nuclease resistance, and improved hybridization with target RNA.

OBJECTS OF THE INVENTION

It is an object of this invention to provide nucleoside analogs wherein the groups linking the normal sugar moieties of nucleosides are substituted with carbonaceous functions such as carbon chain ether functions.

Another object of the present invention is to provide methods for the formulation of improved nucleoside analogs for use in the synthesis of oligonucleosides and otherwise.

Yet another object of the invention is to provide compositions and methods for therapeutics, for diagnoses and for research.

Yet another object is to provide new series of nucleoside analogs including cyclopentane derivatives in lieu of the normal cyclofuranoses.

A still further object yields novel and useful families of nucleoside analogs which may be synthesized through automated processes into oligonucleosides for use in therapeutics, diagnostics, and reagents.

Yet another object is to provide oligonucleotides, analogs and nucleoside precursors for their synthesis which are, at once, substantially non-chiral and non-ionic.

Yet another object is to provide olgonucleotide analogs which are capable of improved cellular uptake, diminished nuclease susceptibility, and improved hybridization with targeted RNA.

These and other objects of the present invention shall become apparent to persons of ordinary skill in the art from a review of the instant specification and appended claims.

BRIEF DESCRIPTION OF THE DRAWINGS

FIGS. 1A through 1D depict a preferred process for effecting the automated synthesis of preferred oligonucleoside analogs.

FIGS. 2 shows a resultant linkage from the process of FIGS. 1A through 1D.

SUMMARY OF THE INVENTION

This invention is directed to the provision of carbon and ether-linked oligonucleosides and their carbocyclic analogs. Alteration of the normal, phosphodiester bonds in oligonucleosides and nucleotides with 2-, and 3-carbon/ether linkages has been found to be likely to yield analogs of nucleosides and nucleotides having improved performance capabilities in many contexts. In particular, it is believe that oligonucleotides prepared from analogs as disclosed by the present invention will demonstrate superior uptake into cells. Additionally, such analogs are believed to be resistant to the effects of nucleases and are likely to lead to improved hybridization with RNA. Moreover, analogs in accordance with the present invention are likely easier to synthesize then are backbones now known for use in nucleosides and nucleotides, especially the phosphate and substituted phosphonate backbones.

The materials of the present invention are amenable to automated synthesis such that a wide variety of the nucleosides and oligonucleotides may be formulated in accordance with this invention. In accordance with the practice of the present invention, oligonucleoside analogs are provided comprising at least two sugar or sugar analog moieties linked together by a group comprising the fomula —O—$R_1$—O— where $R_1$ is a group comprising a two or three carbon backbone. Any sugar which may be used in connection with nucleic acid synthesis may be employed in the present invention. In addition, carbocyclic moieties, especially cyclopentanes, may also be so employed. Heterocyclic bases, especially nitrogen heterocycles, may also find utility in accordance with certain embodiments hereof.

The two or three carbon backbone group which comprises the linking groups for the sugars or sugar analogs may be widely functionalized. Thus, the group may be ethyl, ethylene, acetylene, cyclopropyl, cyclobutyl, ethylenoxy, ethylaziridine and substituted aziridine. Other cyclic structures may also be employed including propyl, isopropyl, methyl-cyclopropyl, $C_3$ through $C_6$ carbocyclic, and 4-, 5-, and 6-membered nitrogen heterocyclic moieties. The two or three carbon linking moiety and the cyclic structures may be widely substituted with amino, hydroxyl, carboxylic acids, and other groups that may enhance oligonucleotide properties such as solubility for formulations and cellular penetration.

Compositions which may be used in formulating the foregoing oligonucleoside analogs are also provided in accordance with this invention. These generally have the structure as follows:

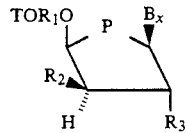

where
P is oxygen or carbon,
$R_1$ is a group comprising a two or three carbon backbone,
T is a selectively removable hydroxyl protecting group,
$R_2$ is a leaving group,
$B_x$ is a variable nucleosidic base or base analog, and
$R_3$ is H, halogen or, preferably, OH.

In accordance with preferred embodiments, the group T is acid labile and the group $R_2$ is amenable to SN-2 displacement when the 3′ carbon of the cyclic structure is attacked by a 4′ nucleophile of a similar moiety. In accordance with other preferred embodiments $R_1$ may be substituted with one or more ionizable functions, especially amino, hydroxyl, and carboxylate functions. Where the moiety is at the terminus of the desired sequence, T is any convenient terminating function such as polyamine or a polyethylene glycol.

Methods for preparing oligonucleoside analogs in accordance with this invention are also provided comprising the steps of providing a nucleoside analog removably attached to a solid support and having a 4′ substituient comprising the structure —O—$R_1$O—T where $R_1$ is a group comprising a two or three carbon backbone, and T is a selectively removable hydroxyl protecting group. The process further comprises removing the hydroxyl protecting group and reacting the deprotected hydroxyl group with a composition having the structure:

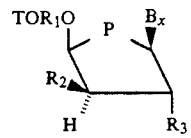

where
P is oxygen or carbon,
$R_1$ is a group comprising a two or three carbon backbone,
T is a selectively removable hydroxyl protecting group,
$R_2$ is a leaving group, and
$B_x$ is a variable nucleosidic base or base analog, and
$R_3$ is H, halogen or, preferably, OH.

Again, in accordance with preferred embodiments, the group T is acid labile and the group $R_2$ is amenable to SN-2 displacement when the 3′ carbon of the cyclic structure is attached by a 4′ nucleophile of a similar moiety. In accordance with other preferred embodiments $R_1$ may be substituted with one or more ionizable functions, especially amino, hydroxyl, and carboxylate functions. Where the moiety is at the terminus of the desired sequence, T is any convenient terminating function such as polyamine or a polyethylene glycol. It is preferred that the deprotected hydroxyl group have its nucleophilicity improved by reacting the composition with a suitable base prior to the nucleophilic displacment.

It is preferred to employ the foregoing process sequentially, a plurality of times, in a manner known to persons of ordinary skill in the art as solid state synthesis in order to provide oligonucleotide analogs of any reasonably desired length and identity.

Oligonucleosides may be prepared in accordance with the foregoing considerations having base units $B_x$ and otherwise being designed so as to hybridize specifically with an RNA, preferably a messenger RNA, of an animal, which is implicated in one or more diseases or abnormal states of that animal. Accordingly, "antisense" hybridization of the oligonucleotide analog with the messenger RNA may take place to cause inactivation of the RNA and modulation of the proteins which it codes. This relationship may also be exploited for purposes of diagnosis. Moreover, the specific hybridization may be used in order to design reagents for nucleic acid research.

DETAILED DESCRIPTION OF THE INVENTION

The phosphodiester structure of ordinary nucleosides and nucleotides is as shown:

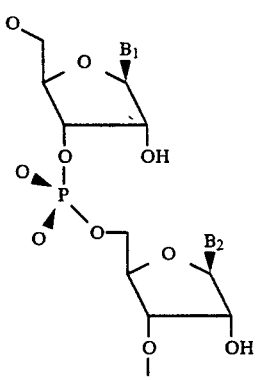

This charged, pro-chiral, structure found in nature, can be used for the synthesis of oligonucleosides or oligonucleoside analogs designed for antisense therapeutics, diagnostics and reagents. Use of this natural formulation, however, does not generally result in particularly useful oligonucleotide species for such purposes. Thus, the charged nature of the phosphodieser group makes admission of the oligonucleotides into the intracellular spaces difficult. Modification of this structure as discussed above, such as the use of sulphur modifications of the phosphorodiester bond structure, moderates the charge involved but leads to chirality in the resulting modified structures. This chirality is thought to effect adversely the entrance of the resulting oligonucleotides into target cells. At the same time, each of these species is liable to hydrolysis by nucleases, ubiquitous in animal cells. Moreover, the sulphur modifications of the linking groups in these nucleotides is believed to interfere with the hybridization of these materials with RNA. Diminished efficacy is the expected result.

In accordance with the present invention, materials having the following general backbone structure are provided.

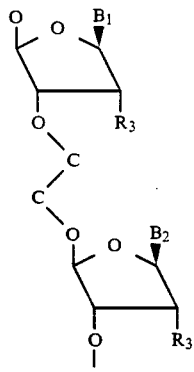

In such molecules, the heteroatom, phosphorus, is eliminated, being replaced by a carbon backbone, preferably one with 2 or 3 carbon atoms, attached to the respective sugar (or sugar analog) moieties such as by preferred ether bonds. It has been found in modeling studies that this structure closely emulates the steric relationships extant in natural, phosphodiester bonds, Accordingly, good hybridization of oligonucleotides prepared with such modifications with messenger RNA is expected. Moreover, since the carbon backbone is, at once, substantially non-ionic and non-chiral, improved transmigration of these modified species into the intracellular spaces is expected. At the same time, it is expected that these improvements will not engender diminution in hybridization such that the present improvements are likely to lead to improved efficacy of drugs, diagnostics, and research reagents employing this type of linking group.

It will be noted that the 5' carbon atom has been replaced. In its stead resides a 4' oxygen function which is attached to the carbon backbone fragment and is, in turn, attached to the 3' position of a second sugar or sugar analog moiety. It has been found that this arrangement does not interfere with the hybridization characteristics of the resulting nucleotides and that same leads to straightforward synthetic techniques as disclosed hereinafter.

A typical synthetic scheme for effecting the linkage of a first sugar or sugar analog with a second is as follows:

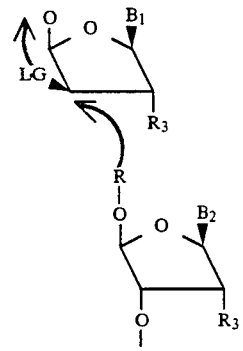

Throughout this specification, the species $B_1$, $B_2$ and $B_x$ refer to either natural or synthetic basis which can be found in a nucleic acid. These would include adenine, thymine, and the other naturally-occurring base moieties together with various simple and complex modifications of such base materials as may be now known or herinafter discovered. While it is preferred that such base moieties be present on the sugars or sugar analogs of the invention during the synthetic schemes depicted herein, such presence is not strictly obligatory as such bases or base analogs may be added subsequent to effecting the linkage between the sugars or sugar analogs.

Similarly, the pattern of hydroxylation, if any, about the sugars and sugar analogs in accordance with this invention is left to the design considerations of the persons skilled in the art. It is generally preferred that a hydoxyl be present at the 2' position ($R_3 = OH$), so as to permit optimum hybridization with targeted RNA. Other functions, especially fluoro, may be used.

In the foregoing scheme, a first sugar or sugar analog having a 4' nucleophilic substituent, "O—R", attached thereto is shown displacing a leaving group from a second sugar or sugar analog moiety. The leaving group participates in an SN-2 reaction with the "O—R" function serving as the nucleophile. A wide variety of nucleophilic groups may be employed in the practice of this invention including the preferred ethoxy group. In another preferred embodiment, the 4'-desmethyl end (the 5'-end of normal oligonucleotides) may be substituted with polyamines or polyethylene glycols for enhanced oligonucleoside properties as set forth in patent application entitled Novel Polyamine Conjugated Oligonucleotides, Ser. No. 558,663, filed Jul. 27, 1990, now U.S. Pat. No. 5,138,045 and incorporated herein by reference.

In accordance with the present invention, methods which are amenable to automated synthetic schemes, especially solid-state synthetic schemes, are preferred. While a number of methodologies may be employed, one preferred methodology follows. A nucleoside analog is attached to a solid support in any conventional fashion. It is customary, and preferred, to employ a linker to a solid support such as a polymeric carrier at the three prime position. This is depicted in FIG. 1A. The moiety is prepared with any base or base analog, $B_x$ and either a furanosyl moiety, where P is oxygen, or cyclopentane function where P is carbon. It is preferred that a 2' hydroxyl function be present ($R_3 = OH$) such that the resulting oligonucleoside will have good hybridization qualities with RNA. The moiety preferably does not have a five prime carbon but rather is substituted in the 4' position as shown in FIG. 1A. Thus, the 4' position is substituted with a hydroxyl ether as shown wherein the hydroxyl function is blocked by a suitable protecting or blocking group T. The group $R_1$ contains a two- or three-carbon backbone chain which may be, optionally, substituted, rendered part of a cyclic structure, or otherwise widely modified. The preferred, 2' hydroxylfunction may be protected as necessary by means well-known to persons of ordinary skill in the art. The only requirement for this function and for its protection is that the same be designed so as not to interfere with the substantive reactions in accordance with this invention.

A number of functional groups may serve for the protection of the primary hydroxyl of the hydroxyether function on the four prime position. Thus, the group T may comprise any blocking or protecting group which is selectively removable and which otherwise is consistent with the reaction schemes set forth herein. It is preferred that such blocking groups be acid labile under relatively mild conditions. Thus, tetrahydropyranyl, tert-butyl, bis-(p-methoxyphenyl) phenylmethyl (DMT), groups may be so used, as may others. It is preferred that the tert-butyl group be employed. The protecting group T is removed such as under acidic conditions to liberate the free hydroxyl group. The free hydroxyl group is then preferably treated with a base having characteristics suitable to render the primary hydroxyl into a good nucleophilic species. Wide varieties of such bases may be so employed including sodium hydride, Grignard reagents, especially methylmagnesium chloride, t-butyl magnesium chloride, lithium diisopropyl amide, methyl lithium, n-butyl lithium and DBU. Anhydrous conditions are generally required.

This reaction takes place in any suitable solvent, preferably in aprotic solvents such as acetonitrile, tetrahydrofuran or dioxane. Such treatment affords species shown in FIG. 1B which is still attached to the solid support. This active species is then reacted with a monomeric unit as shown in FIG. 1C. Once again, the monomeric unit may be either a furanosyl or a cyclopentyl moiety as may be desired. The base or base analog unit is again represented by the term $B_x$ with the understanding that any base, modified base or base analog may be so selected. Once again, a 2' hydroxyl function is preferred. A 4' protected hydroxy ether is again provided including a two- or three- carbon backbone containing group. This functionality may be either the same or different from the one selected in the previous step and indeed a number of variations may be employed within a single oligonucleoside. For purposes of illustration, however, the same group, $R_1$ has been depicted in FIG. 1. A further functionality is provided in such monomers at the 3' position. Thus, an $\alpha$-3' leaving group, $R_2$ is provided. This leaving group is capable of participating in SN-2 reactions with the nucleophilic species as shown. Exposing the nucleophile of FIG. 1B to the monomer of FIG. 1C results in a nucleophilic displacement reaction on the 3' position of the monomer. This is depicted in FIG. 1D so as to result in the linking of the two sugars or sugar analogs. This linkage comprises the diether comprising the two- or three-carbon unit $R_1$ with appended functions if any.

As will be appreciated by persons of ordinary skill in the art, this procedure may be repeated sequentially in order to build up oligonucleosides of any reasonably desired length. A number of monomeric species may be inserted into the chain such that varying numbers of bases $B_x$, varying hydroxylic substituients at the two prime carbon atom, and varying linking functions $R_1$ may be incorporated. Additionally, mixtures of oxygencycles and carbon-cycles may be used as desired. Accordingly, it should be appreciated that this reaction scheme is quite general and will likely be appropriate for a whole host of substituients on the monomers.

The growing oligomer may be terminated at any convenient spot and removed from the support in the conventional way. The result of this synthetic scheme is depicted in FIG. 2. A fragment of the oligonucleoside is shown wherein two sugar or sugar analog species are united by a linking group. Since the same preferably have base units $B_x$ attached thereto, the same may be seen to be an oligonucleotide analog.

The leaving groups $R_2$, which are preferred for use in the present invention comprise any leaving group which is capable of SN-2 displacement on the 3' carbon. Preferred among such leaving groups are trifluoromethylsulfonyl (triflate), methylsulfonyl (mesyl), halogens, o-trichloro acetimidates, acyloxy, and 2,4,6-trichlorophenyl, with the first two groups being most preferred.

As will be also appreciated by persons skilled in the art, various ancillary steps may also be taken in furtherance of the present invention. Thus, washing, neutralizing and other reactions or steps may be employed in order to maximize the efficiency and yield of these processes. Additionally, each step may be performed a plurality of times in order to ensure substantial completeness of the addition of each nucleoside subunit. It will be appreciated that a number of other reaction schemes may be employed in order to provide two- and three- carbon backbone-containing linking groups between sugars and sugar analogs of nucleic acid species in accordance with the present invention. It is similarly understood that functions other than ether functions including amide, sulfide and the like may also be employed in conjunction with certain embodiments of the invention.

Oligonucleotide analogs formed from nucleosides in accordance with the present invention may be used in therapeutics, as diagnostics, and for research. Copending applications for United States Letters Patent, assigned to the assignee of this invention, and entitled Compositions and Methods for Modulating RNA Activity, Ser. No. 463,358, filed Jan. 11, 1990, now abandoned; Antisense Oligonucleotide Inhibition of Papillomavirus Ser. No. 445,196 Filed Dec. 4, 1989; Oligonucleotide Therapies for Detecting and Modulating the Effects of Herpesvirus, Ser. No. 485,297, Filed Feb. 26, 1990; Reagents and Methods for Modulating Gene Expression Through RNA Mimicry Ser. No. 497,090, Filed Mar. 21, 1990, now abandoned; Oligonucleotide Modulation of Lipid Metabolism, Ser. No. 516,969, now abandoned, Filed Apr. 30, 1990, now abandoned; Antisense Inhibitors of the Human Immunodefiency Virus, Ser. No. 521,907, Filed May 11, 19990, now U.S. Pat. No. 5,166,195, Nuclease Resistant Pyrimidine Modified Oligonucleotides That Detect and Modulate Gene Expression, Ser. No. 558, 806, now abandoned, filed Jul. 27, 1990; Novel Polyamine Conjugated Oligonucleotides, Ser. No. 558,663, now U.S. Pat. No. 5,138,045 Filed Jul. 27, 1990; and Modulation of Gene Expression Through Interference with RNA Secondary Structure, Ser. No. 518,929, filed May 4, 1990, now abandoned, discloses a number of means whereby improved modulation of RNA activity may be accomplished through oligonucleotide interaction. Each of the structural modifications and each of the processes disclosed therein may be used in conjunction with the compositions and methods of the present invention and all such uses and combinations are envisioned herein. Accordingly, the disclosures of the foregoing United States patent applications are incorporated herein by reference. Similarly, the modification set forth herein may be employed in conjunction with the inventions of the foregoing applications.

In accordance with the present invention, a wide variety of groups, herein generally denominated $R_1$, may be employed for use as linkers herein. Such species generally comprise two- and three-carbon backbone units. Among the materials which are preferred for use in accordance with certain embodiments of this invention as the linkers $R_1$ are ethyl, ethylene, acetylene, cyclopropyl, cyclobutyl, ethleneoxy, ethyl aziridine, and substituted ethyl aziridine. Other moieties which are useful include propyl, isopropyl, methyl-cyclopropyl, $C_3$ through $C_6$ carbocyclic, and 4- 5-, and 6- membered nitrogen heterocyclic moieties. The term "two- and three- carbon backbone as used in the present invention means that there is a chain of two or three carbon atoms between the atoms connecting the four prime position of one sugar and sugar analog and the atom connecting the linker to the three prime position of a second sugar or sugar analog. To avoid any ambiguity, it will be understood that the cyclopropyl function meets this test since a two carbon chain, the backbone, exists although a one carbon unit also exists. A cyclohexyl functionality, connected 1,2- would similarly meet this test since although a four carbon unit connects the end points, a two carbon chain also exists.

The two or three carbon linking moiety and the cyclic structures may be widely substituted with amino, hydroxyl, carboxylic acids, and other groups that will enhance oligonucleotide properties such as solubility for formulations and cellular penetration.

A full evaluation of all of the many substituients, heterocycles, and other species which may form the linkers in accordance with the present invention has not yet been made. It will be understood that all such functionalities may be comprehended hereby so long as the foregoing, overall considerations are met.

EXAMPLES

The present invention will now be illustrated by example. It will be understood that this invention is not to be considered to be limited by the exemplary material but solely by the appended claims.

EXAMPLE 1

Carbocyclic 4'-Desmethyl Ribo-or-2 $\alpha$-Deoxynucleosides

A. CPG Bound Carbocyclic Desmethyl-ribo-or-2'deoxy-nucleoside 3-(Aden-9-yl)-5-hydroxy-1,2-cyclopentene, obtained from the coupling of cyclopentene epoxide and adenine according to the method of Trost et. al. is successively silylated, benzoylated, and tritylated according to standard procedures to provide 3-(6-benzoyladenyl)-5-triphenylmethoxyl-1,2-cyclopentene. Cis-hydroxylation and selective t-butyldimethylsilylation provides the 2'-O-t-butyldimethylsilyl derivative. The free 3'-hydroxy of this carbocyclic nucleoside is attached to control-glass pore silica gel (CPG) according to the standard procedure of T. Atkinson and M. Smith (Oligonucleotide Synthesis. A Practical Approach. M. J. Gait, Ed., IRL Press, Washington, D.C., 1985, p 49). The CPG-bound carbocyclic adenine is treated with acid to remove the 4'-O-trityl protection and the resulting hydroxy group is subsequently reacted with t-butoxyethyl bromide and base to afford the 4'-O-t-butoxyethyl derivative. The final product, 4'-desmethyl-4'-O-t-butoxyethyl -2't-butyldimethylsilyl-3'-CPG-N6-benzoyl adenine, is placed in a column and attached to a ABI-380B automated DNA Synthesizer or a 7500 Milligen/Biosearch DNA Synthesizer. The CPG-bound 4'-desmethyl ribonucleosides can be converted to their 2'-deoxy forms by the successive treatment of the polymer with tetrabutyl ammonium fluoride, thiocarbonylimidazole, and tributyl tin hydride. These procedures are appropriate for the preparation of CPG bound carbocyclic 4'-desmethyl derivatives of the other natural occurring bases or nucleic acids base analogs.

B. Carbocyclic Desmethyl-ribo-monomers—First Procedure 3-(Aden-9-yl)-5-hydroxy-1,2-cyclopentene, obtained from the coupling of cyclopentene epoxide and adenine according to Trost et al. is successively silylated, benzoylated, and tritylated according to standard procedures to provide 3-(N6-benzoyladenyl)- 5-triphenylmethoxyl -1,2-cyclopentene. Cis-hydroxylation and selective t-butyldimethylsiylation provides the 2'-O-t-butyldimethylsilyl derivative. This material is treated with trichloro-acetonitrile and sodium hydride in dry acetonitrile to afford the a trichloroacetimidate with is subsequently SN2 displaced by water. Preparation and reactivity of trichloroacetimidates has been described. The resulting $\beta$-3'-hydroxyl group is activated for SN-2 reaction by the action of trichloroacetonitrile/sodium hydride. The $\beta$-3'-hydroxy group may also be activated for SN2 reactions by the treatment with trifluoromethanesulfonic acid anhydride and pyridine. This procedure provides the triflate group in the 3'-position of the 4'-desmethyl-4'-O-t-butoxyethyl-2'-t-butyldimethylsilyl-N6-benzoyl adenine. This procedure is of a general nature and can be applied to the synthesis of any carbocyclic 4'-desmethyl-ribonucleoside.

C. Carbocyclic Desmethyl-ribo-monomers—Second Procedure

The carbocyclic nucleoside antibiotic (−)-neplanocin A, obtained from fermentation or total synthesis; C.

R. Johnson, et. al., Tetrahedron Letters, 28, 4131–4134, (1987); base analogs of (−)-neplanocin; A, K. Biggadike, et al., Jorunal Chemical Society, Chemical Communication, 458 (1990) as its N6-benzoyl derivative is reduced with a borane reagent and then protected as its isopropylidine. The unprotected 5'-hydroxyl is oxidized with oxygen and platinum oxide, and subsequent, reductive decarboxylation with lead tetraacetate provides 4'-desmethyl carbocyclic adenosine. This oxidation/reduction closely follows a known procedures. The 4'-desmethyl carbocyclic adenosine 2,3- isopropylidine is successively treated with t-butoxyethyl bromide and pyridine, mild acid, ant t-butyldimethysilyl chloride in pyridine to afford the 4'-desmethyl carbocyclic derivative with an α-3'-hydroxyl group unprotected. This intermediate was described in paragraph A. Conversion into an activated β-3'-leaving group is described in paragraph B.

D. Carbocyclic Desmethy-2-deoxyribo-monomers 4-p-Tosylate-1,2-cyclopentene is treated with appropriately protected bases to afford cyclopentenylated bases of the natural nucleoside bases or analogs of the nucleic acids bases. Hindered face (β-face) hydroxylation provides 3,4-dihydroxy cyclopentyl-protected bases which are treated with t-butoxyethyl bromide and the isomers are separated by chromatography. The appropriate isomer is treated with trichloro- acetonitrile and sodium hydride in acetonitrile to provide 4'-desmethyl-4'-O-t-butoxyethyl-3'-O-trichloroacetimidyl-2'-deoxy carbocyclic nucleosides.

EXAMPLE 2

Synthesis of 4'-Desmethyl Ribo-or-2'-Deoxy-Nucleosides

A. CPG Bound Desmethyl-ribo-or-2'-deoxyribo-nucleosides—First Procedure

Commercially available CPG-bound ribo or 2'-deoxyribonucleosides are treated with oxygen saturated acetonitrile and platiunum oxide to provide the 4'-desmethyl-4'-carboxylate derivative. The CPG column is treated with lead tetraacetate to reductively decarboxylate the bound nucleoside. The resultant 4'-hydroxyl group is alkylated with t-butoxyethyl bromide in pyridine to provide CPG-bound 4'-desmethyl-4'-O-t-butoxyethyl-2'-deoxy (or 2'-t-butyldimethylsilyl) nucleosides.

B. CPG Bound Desmethyl-ribo-or-2'-deoxyribo-nucleosides—Second Procedure

Commercially available ribo or 2'-deoxy-ribonucleosides protected in the heterocycle and 2', 3'-O-positions or the 3'-O-position by standard procedures such as the 2',3'-O- isopropylidinyl or 3'-O-benzoyl were successively oxidized and reductively decarboxylated with oxygen/platinum oxide and LTA to afford a 4'-hydroxyl group. These protected nucleosides are converted to their 4'-desmethyl-4'-O-t-butoxyethyl derivatives by treatment with t-butoxyethyl bromide and pyridine. Removal of the 3'-O-benzoyl or 2',3'-O-isopropylidine groups and subsequent attachment to control glass pore silica gel according to standard procedures provides CPG-bound desmethyl-ribo-or2'-deoxyribonucleosides suitable for solid phase, automated nucleic acids syntehesis.

C. 4'-Desmethyl ribo-and 2'-deoxyribo monomers

Commercially available 2'-deoxyfuranosyl nucleosides and xylofuranosylnuclosides with appropriate base protection are selectively tritylated in the 5=-position then mono or di-benzoylated in the sugar ring. The nucleosides are now treated with acid to remove the trityl protection. The successive action of oxygen/PtO2 and LTA provides the 4'-desmethyl nucleosides which are subsequently alkylated with t-btoxyethyl bromide. Basic deprotection of the nucleosides affords the 4'-desmethyl-2'-deoxylyxofuranosylnucleosides and the 4'-desmethylxylo nucleosides. The 4'-desmethyl-2'-deoxylyxo nucleoside is treated with trichloroacetonitrile and sodium hydride to activate the 3'-up hydroxyl group to SN2 reactions. The 4'-desmethylxylo nucleoside is selectively t-butyldimethylsilylated at the 2'-position and then is treated with trichloroacetonitrile and sodium hydride to activate the 3'-up hydroxyl group to SN2 reactions. The triflate leaving group in the 3'-up position of there nucleosides can also be readily prepared.

EXAMPLE 3

Synthesis of Carbocyclic 4'-Desmethyl Ribo-or-2'-Deoxy-Oligonucleosides and 4'-Desmethyl Ribo-or-2'-Deoxy-Oligonucleosides Linked Via an Ethylene Glycol The appropriately CPG-bound 4'-desmethylnucleoside (ribo or 2'-deoxyribo or carbocyclic ribo or 2'-deoxyribo) that will become the 3'-terminal base is placed in an Applied Biosystems, Inc. (ABI) column and attached to an ABI 380B automated DNA Synthesizer. The automated (computer controlled) steps of a cycle that is required to couple a desmethyl nucleoside unit to the growing chain is as follows.

| STEP | REAGENT OR SOLVENT MIXTURE | TIME (min/sec) |
|---|---|---|
| 1. | Dichoroethane | 2:30 |
| 2. | 3% DCA in dichloroethane | 3:00 |
| 3. | Dichloroethane | 1:30 |
| 4. | Tetrahydrofuran | 1:30 |
| 5. | 3.0 Molar methylmagnesium chloride in THF | 1:00 |
| 6. | Tetrahydrofuran | 1:00 |
| 7. | 4'-Desmethyl-4'-O-t-butoxyethyl 3'-up trichloroacetimidate nucleoside 10 equivalents to CPG-bound nucleoside | 2:00 |
| 8. | Recycle to step 7 | 2:00 |
| 9. | t-Butyldimethylsilyl chloride/ pyridine | 2:00 |
| 10. | Recycle - go to step one | |

At the completion of the synthesis, the deprotection/purification process is as follows:

| STEP | REAGENT OR SOLVENT MIXTURE | TIME (min/sec) |
|---|---|---|
| 1. | 3% DCA in dichloroethane | 3:00 |
| 2. | Acetonitrile wash | 3:00 |
| 3. | Tetrabutyl ammonium fluoride 1.0 molar solution in THF | 5:00 |
| 4. | Acetonitrile | 2:00 |
| 5. | 15% Ammonium hydroxide/ethanol (1:1), 50° C. | 5:00 |
| 6. | Filter, wash CPG resin with 15% NH4OH/EtOH | |
| 7. | 30% NH4OH, 50° C. | 24 hr |
| 8. | Evaporate solution to dryness | |

EXAMPLE 4

Preparation of Polyamine and Polyethylene Glycol Derivatives of Carbocyclic 4'-Desmethyl Ribo-or-2'-Deoxy-Oligonucleosides and 4'-Desmethyl Ribo-or-2'-Deoxy-Oligonucleosides Linked Via an Ethylene Glycol At the completion of the synthesis, polyethylene glycols (PEGs) with terminal alkyl bromides or phthaloyl and trifluoroacetyl protected polyalkyl amines with terminal alkyl bromides are reacted with the CPG-bound oligonucleoside in the presence of base. Deprotection, workup, and purification provides 4'-polyethylene glycol or 4'-polyamines nucleosides and carbocyclic nucleosides linked via ethylene glycol moieties.

What is claimed is:

1. A composition of matter having the structure

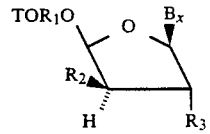

where:
   $R_1$ is selected from the group consisting of ethyl, ethylene, acetylene, cyclopropyl, cyclobutyl, ethyleneoxy, ethyl aziridine, and ethyl aziridine substituted with amino, hydroxyl or carboxylic acid groups,
   T is selected from the group consisting of tetrahydropyranyl, tert-butyl and bis-(p-methoxyphenyl)-phenylemthyl,
   $R_2$ is selected from the group consisting of trifluoromethylsulfonyl, methylsulfonyl, halogen, o-trichloroacetimidates, acyloxy, and 2,4,6-trichlorophenyl, $B_x$ is a nucleosidic base, and
   $R_3$ is OH, halogen, or H.

2. The composition of claim 1 wherein $R_1$ is ethyleneoxy.

3. The composition of claim 1 wherein T is tert-butyl.

4. The composition of claim 1 wherein $R_2$ is trifluoromethylsulfonyl or methylsulfonyl.

5. The composition of claim 1 wherein $R_3$ is hydroxyl.

6. The composition of claim 1 wherein $R_1$ is ethyleneoxy, T is tert-butyl, $R_2$ is trifluoromethylsulfonyl or methylsulfonyl, and $R_3$ is hydroxyl.

* * * * *

UNITED STATES PATENT AND TRADEMARK OFFICE
CERTIFICATE OF CORRECTION

PATENT NO. : 5,223,618
DATED : June 29, 1993
INVENTOR(S) : Cook et al.

It is certified that error appears in the above-identified patent and that said Letters Patent is hereby corrected as shown below:

In column 2, line 32 delete "olgonucleotide" and insert --oligonucleotide--.

In column 5, line 23, delete "phosphodieser" and insert --phosphodiester--.

In column 7, line 27, delete " hydroxylfunction" and insert --hydroxyl function--.

In column 10, line 14, delete "3-(6-benzoyladenyl)" and insert --3-(N6-benzoyladenyl)--.

In column 10, line 48, delete "t-butyldimethylsiylation" and insert --t-butyldimethylsilyation--.

In column 11, line 3, delete "Jorunal" and insert --Journal--.

In column 11, line 13, delete "ant" and insert --and--.

In column 11, line 42, delete "platiunum" and insert --platinum--.

In column 12, line 4, delete "xylofuranosylnuclosides" and insert --xylofuranosylnucleosides--.

In column 12, line 10, delete "t-btoxyethyl" and insert --t-butoxyethyl--.

UNITED STATES PATENT AND TRADEMARK OFFICE
CERTIFICATE OF CORRECTION

PATENT NO. : 5,223,618

DATED : June 29, 1993

INVENTOR(S) : Cook et al.

It is certified that error appears in the above-identified patent and that said Letters Patent is hereby corrected as shown below:

In column 14, line 9, after "where", delete ":" and insert --P is oxygen--.

In column 14, line 22, before "$R_3$" insert --$B_x$--.

Signed and Sealed this

Twenty-fifth Day of October, 1994

Attest:

BRUCE LEHMAN

Attesting Officer

Commissioner of Patents and Trademarks